United States Patent [19]

Stein

[11] 4,277,609
[45] Jul. 7, 1981

[54] SYDNONE IMINES

[75] Inventor: Reinhardt P. Stein, Audubon, Pa.

[73] Assignee: American Home Products Corporation, New York, N.Y.

[21] Appl. No.: 171,423

[22] Filed: Jul. 29, 1980

Related U.S. Application Data

[63] Continuation-in-part of Ser. No. 71,606, Aug. 31, 1979, abandoned.

[51] Int. Cl.³ .................. A61K 31/42; C07D 271/04
[52] U.S. Cl. ................................ 548/125; 424/272
[58] Field of Search ......................... 548/125

[56] References Cited

U.S. PATENT DOCUMENTS 3,277,108  10/1966  Daeniker et al. ............... 548/125

FOREIGN PATENT DOCUMENTS 2028880  6/1970  Fed. Rep. of Germany .
2738022  6/1978  Fed. Rep. of Germany .
329890   4/1972  U.S.S.R. .
222370   8/1973  U.S.S.R. .

OTHER PUBLICATIONS

Burger, A., "Medincinal Chemistry," Second Ed., Inter. Sci., New York (1960) p.42.
Kholodov, et al. "Chem. Abst.," vol. 78, (1973), 119341n, from Khim-Farm. Zh. 1973, 7(1), 50-2.
Goodman et al., "The Pharmacological Basis of Therapeutics," 3rd Ed., pp. 484–486.
Polgar et al., "Acta Pharm. Hung." 41, Suppl. (1978) pp. 23–24, and Translation.
Polgar et al., "Xenobiotica," (1979), vol. 9, No. 8, pp. 511–520.
Kholodov et al., "Mater Resp. Rass his Konf Farmacol Gruz," 2nd (1977) pp. 84–85 and Translation.
Yashunskii et al., "J. Med. Chem.," vol. 14, (1971) pp. 1013–1015.
Olovyanishinkiva et al., "Khim. Geterotsikl Suedin," vol. 2, (1978), pp. 170–175.
Olovyanishinkiva et al., "Khim. Geterotsikl Suedin," vol. 9, (1975), 1198–1203.
Polgar et al., "Chem. Abst.," vol. 92, (1980) 121476t, from Xenobiotica, (1979), 9(8) 511–520 (Eng.).

Primary Examiner—Anton H. Sutto
Attorney, Agent, or Firm—Richard K. Jackson

[57] ABSTRACT

A compound of the formula:

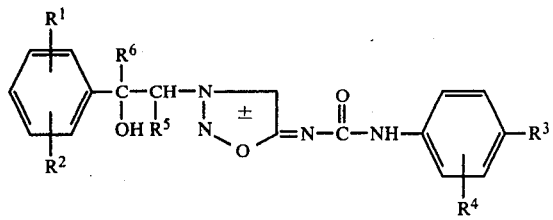

in which the enantiomeric form is d,l or l- when $R^5$ is hydrogen and d,l or l-threo when $R^5$ is other than hydrogen;

$R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms or alkoxycarbonyl of 2 to 4 carbon atoms;

$R^3$ is hydrogen, halo, nitro or alkanoyl of 2 to 4 carbon atoms;

$R^5$ and $R^6$ are, independently, hydrogen or methyl;

or a non-toxic acid addition salt thereof, are central nervous system stimulants.

15 Claims, No Drawings

SYDNONE IMINES

This application is a Continuation-in-part of Ser. No. 071,606, filed Aug. 31, 1979. now abandoned.

BACKGROUND OF THE INVENTION

After the discovery of the central nervous system stimulatory properties of 3-(1-methyl-2-phenylethyl)-N-(phenylcarbamoyl)sydnone imine (Sydnocarb; U.S.S.R. 329,890 and Offenlegungsschrift 2,028,880) various analogues have been reported. U.S.S.R. 222,370 and Offenlegungsschrift No. 2,738,022 disclose sydnone imines which contain phenyl, 1- or 2-phenylethyl and the phenylisopropyl groups in 3-position as well as N-meta- and para-chlorophenyl and N-phenyl carbamoyl groups. Variations of 3-benzyl sydnonimines are disclosed in U.S. Pat. No. 3,277,108. Other variously substituted 3-aralkyl sydnonimines are disclosed by Olovyanishinkiva et al., Khim. Geterotsikl Soedin, 2 170–175 (1978) and 9 1198–1203 (1975).

Sydnocarb is conventionally produced by cyanomethylation of amphetamine followed by nitrosation and ring closure with a mineral acid to yield sydnophen as an acid halide salt which is reacted with phenylisocyanate under mildly basic conditions to introduce the N-phenylcarbamoyl group. As an asymmetric compound, amphetamine may be employed as the initial reactant as the racemic d,l-mixture or as the pure d- or l-isomer to yield racemic or optically active sydnophen and ultimately sydnocarb.

Yashunskii et al., J. Med. Chem., 14 1013–1015 (1971) disclose the marked CNS-stimulatory effect of 3-(1-methyl-2-phenylethyl) sydnonimine (Sydnophen). The relative activities of a large number of alkyl, aryl and aralkylsydnonimines are presented in Table 1 on page 1014. Most of them, including compound XVIII (2-hydroxy-1-methyl-2-phenylethyl-sydnonimine), were essentially inactive central nervous system stimulants relative to compound XIII (Sydnophen), demonstrating the criticality of the structure of the 3-substituent in the Sydnocarb series of compounds as far as CNS stimulatory activity is concerned. Thus, although the activity profile of Sydnocarb is not identical to that of amphetamine, or for that matter Sydnophen, CNS stimulatory activity is a common property of the initial reactant amphetamine, the intermediate Sydnophen and the final product Sydnocarb.

The metabolites of Sydnocarb have been studied by several groups, L. E. Kholodov and E. T. Lilin, Mater. Resp. Rasshir. Konf. Farmacol. Gruz. 2nd 1977, 84–5 report finding hydroxylation of Sydnocarb at the beta carbon of the phenylisopropyl substituent and at the phenyl ring of the phenylcarbamoyl group, hydrolytic cleavage of the phenylcarbamoyl group and ring opening of the heterocyclic nucleus. They report that the psychostimulating activity of Sydnocarb is a property of that compound and not its metabolites. Polgar et al. Acta. Pharm. Hung., 48, Suppl. 23–24 (1978) and Xenobiotica 9, No. 8, 511–520 (1979) report several hydroxylated metabolites and conjugates, but does not report finding beta-hydroxysydnocarb as an entity.

DESCRIPTION OF THE INVENTION

In accordance with this invention there is provided a group of central nervous system stimulants which are 3-(2-hydroxy-2-phenylethyl)-N-[(phenylamino)carbonyl]sydnonimines optionally substituted in either or both phenyl rings, of the formula:

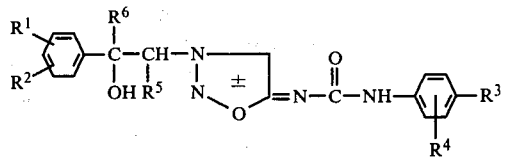

in which the enantiomeric form is d,l or l- when $R^5$ is hydrogen and d,l or l-threo when $R^5$ is other than hydrogen;

$R^1$ and $R^2$ are, independently, hydrogen, alkyl of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;

$R^3$ is hydrogen, halo, nitro or alkanoyl of 2 to 4 carbon atoms;

$R^4$ is hydrogen, halo, nitro or perfluoroalkyl of 1 to 3 carbon atoms;

$R^5$ and $R^6$ are, independently, hydrogen or methyl or a non-toxic acid addition salt thereof.

It is generally preferred that the halo substituent be chlorine, bromine or fluorine although iodine is acceptable. Likewise, it is preferred that the alkyl and alkoxy substituents be relatively small, the methyl, ethyl, propyl, isopropyl, methoxy, ethoxy, propoxy and isopropoxy groups being preferred. The $R^3$ substituent in 4 position when $R^4$ is hydrogen influences potency to a greater extent than $R^1$, $R^2$ and $R^4$ and is preferably a halogen. The non-toxic acid addition salts of the compounds of this invention are conventionally produced by the method and from any of the acids disclosed in U.S. Pat. No. 3,277,108. The adduct products are preferably formed with hydrochloric, hydrobromic, sulfuric, phosphoric, acetic, propionic, oxalic, succinic or maleic acid.

The 3-(2-hydroxy-2-phenylethyl)sydnonimine compounds of this invention contain a chiral center at the benzylic carbon atoms and appear as the racemic d,l-mixture which is resolvable into the pure d- and l-isomers. The l-isomer possesses substantially all of the CNS stimulatory activity and is preferred over the racemic mixture for that reason. Unlike Sydnocarb, the compounds of this invention are derived from a phenylethanolamine or a phenylpropanolamine through the intermediate 3-(2-hydroxy-2-phenylethyl)sydnonimine or 3-((2-hydroxy-1-methyl-2-phenylethyl)sydnonimine, none of which demonstrate any meaningful central nervous system stimulatory activity. Being derived from reactants and through intermediates which are substantially devoid of activity, the compounds of this invention do not share with Sydnocarb the potential problem of degradative reversion or metabolic conversion back to a precursor which is itself active with a different pharmacological profile. Furthermore, handling of the inactive reactants and/or intermediates involved in this invention poses no problem for the production chemist.

The 3-[(2-hydroxy-1-methyl-2-phenylethyl)]sydnonimines and the 3-[(2-hydroxy-2-methyl-1-methyl-2-phenylethyl)]sydnonimines of this invention contain two chiral centers and provide two racemic mixtures of product. Of the four optically active isomers only the l-threo isomer is meaningfully active as a central nervous system stimulant.

The activity profile of the compounds of this invention is similar to that of amphetamine in some aspects while being devoid of other activities of amphetamine. For example, like amphetamine the compounds of this invention increase motor activity. However, the compounds of this invention are much less toxic than amphetamine, providing a slower onset of activity (which indicates less euphoria and abuse potential).

The compounds of this invention were shown to possess central nervous system stimulant activity by subjecting them to the following standard test procedure:

Male mice weighing 17 to 25 gms. are injected orally with drug solubilized or suspended in 1% Tween ® 80. Control animals are injected with 1% Tween ® 80.

Six Columbus Instrument Company activity chambers are employed. Three mice given identical treatment are placed in each chamber for all tests. During each run, control animals (1% Tween ® only) occupy 3 chambers; the other 3 chambers measure activity of drug treated animals. For each dose of a given drug the experiment is run two times in a counterbalanced design so that each specific activity chamber records the activity of control animals during one run, and the activity of drug animals on the other run. Thus at each dose level 18 mice are used in the drug group and 18 mice in the control group.

Activity counts are recorded every ten minutes for a period of 2 hours. The data are analyzed using Students "t" test comparing the means of the control and drug groups for each 10 minute period. The drug treated group is compared graphically with the control group in regard to duration of action and dose response at peak drug activity.

As central nervous system stimulants with unique activity profiles, the compounds of this invention are useful in the treatment of anergic disorders (such as sleepiness and fatigue) including related types of depression and narcolepsy. Based upon the potency of the compounds of this invention in use in mice, the does contemplated for use in the 70 kilogram human would vary from about 35–700 milligrams administered orally once or twice per day under the guidance of a physician. Of course, the dosage regimen as well as the route of administration, oral or parenteral, will vary with the condition of the patient relative to age, severity of depression, etc.

The compounds of this invention are prepared by conventional techniques analogous to those employed in the preparation of Sydnocarb. Thus, a properly substituted phenylethanolamine is cyanomethylated with a reactant $XCH_2CN$ where X may be —OH, —Br, —Cl, tosyl, and the like to form the intermediate

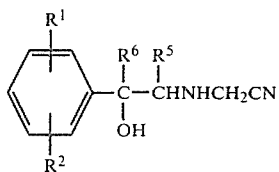

which is nitrosated with an excess of $NaNO_2$ in aqueous HCl to yield

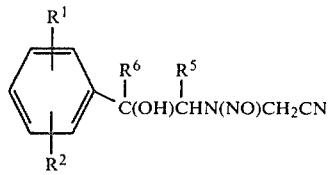

which upon treatment with HCl (anhydrous or in an alkanol, preferably isopropanol) yields the sydnonimine salt

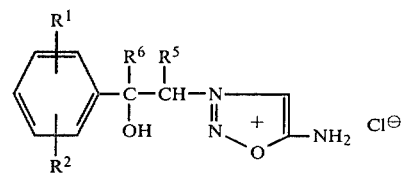

which when reacted as an alcoholic suspension (methanol, ethanol, isopropanol, etc.) with

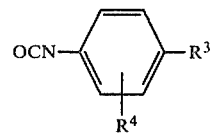

in the presence of a mild base such as sodium acetate yields the desired 3-(2-hydroxy-2-phenylethyl)-N-[(phenylamino)carbonyl]-sydnonimine derivatives. The mild base releases the reactive sydnone free base

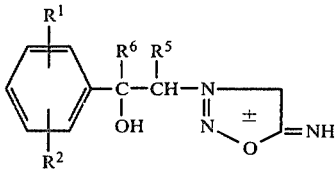

which readily undergoes nucleophilic addition to the isocyanate reactant. Alternatively and preferably the compounds of this invention, where $R^6$ is other than hydrogen, may be prepared directly by reaction of the appropriate nitroso-nitrile with an appropriately substituted aryl isocyanate in the presence of an organic amine base, such as triethylamine, 4-dimethylaminopyridine, and the like, following the procedure disclosed in Offenlegungsschrift No. 2,738,022.

The following examples illustrate without limitation the process for producing the compounds of this invention. Where the intermediate cyanomethylated product of phenylethanolamine and the N-nitroso derivative thereof are isolated as oils, no attempt was made to obtain the purified intermediate. The activity counts presented at the end of each example represent the difference from control based upon the test procedure disclosed, supra. Sydnocarb itself demonstrated a difference from control of 939 activity counts at 10 mg/kg.,

EXAMPLE 1 dl-[(2-Hydroxy-2-phenylethyl)amino]acetonitrile, hydrochloride

Dissolve dl-2-amino-1-phenylethanol (5.49 g.; 0.04 moles) in ethyl acetate (25 ml) then add a solution of cyanomethyl p-toluenesulfonate (4.22 g.; 0.02 moles) in ethyl acetate (25 ml). Allow the reaction to stand at room temperature overnight then filter and evaporate the solvent from the filtrate in vacuo. Dissolve the resulting oil in hot diethyl ether, treat with decolorizing charcoal, filter and evaporate the ether in vacuo. Dissolve the oil in ethyl acetate and add an excess of 5 N isopropanolic-HCl solution (i.e. more than 4 ml), scratch to initiate crystallization and let stand to complete crystallization. Filter to obtain 3.08 g. of the title product, m.p. = 143°–145° C.

Analysis for: $C_{10}H_{12}N_2O \cdot HCl$: Calculated: C, 56.47; H, 6.16; N, 13.17; Cl, 16.67: Found: C, 56.40; H, 6.16; N, 13.09; Cl, 16.54.

Combine dl-2-amino-1-phenylethanol (5.49 g.; 0.04 moles) with water (60 ml) and 5 N aqueous HCl (8 ml; 0.04 moles) then stir until clear. Add 37% aqueous formaldehyde solution (4 ml), then with stirring drip in a solution of potassium cyanide (2.61 g.; 0.04 moles) in water (20 ml). Stir a further 3 hours at room temperature then add diethyl ether and let stand overnight. Extract with diethyl ether, wash, dry and evaporate the solvent in vacuo. Purify the resulting oil and convert to the HCl salt as in the preceding paragraph to obtain 4.10 g. of the title product, m.p. = 146°–148° C.

EXAMPLE 2 dl-5-Amino-3-(2-hydroxy-2-phenylethyl)-1,2,3-oxadiazolium chloride

Cover dl-[(2-hydroxy-2-phenylethyl)amino]acetonitrile, hydrochloride (10.63 g.; 0.05 moles) with water (15 ml), add 5 N aqueous HCl (30 ml; 0.15 mole) and ethanol (45 ml) and stir until clear. Cool the reaction to below 0° C. then with stirring drip in a solution of sodium nitrite (6.90 g.; 0.10 moles) in water (35 ml). Let stir, warming to room temperature for 3 hours. Add brine and extract with diethyl ether. Wash, dry and evaporate the extract in vacuo. Treat the resulting oil in diethyl ether with decolorizing charcoal, filter and remove the solvent in vacuo to obtain dl-N-nitroso-N-(2-hydroxy-2-phenylethyl) amino acetonitrile as an oil. Dissolve the oil in ethyl acetate and add excess 5 N-isopropanolic-HCl (over 10 ml). Filter the resulting crystalline solid to obtain 8.94 g. of title product, m.p. = 164°–170° C. (dec.). Dissolve the solid in boiling methylene chloride-methanol and replace the solvents with isopropanol by boiling on the steam-bath. Cool and let crystallize, then filter to obtain 5.42 g. of pure title product, m.p. −171°–174° C. (dec.).

Analysis for: $C_{10}H_{12}ClN_3O_2$: Calculated: C, 49.69; H, 5.01; N, 17.39; Cl, 14.67%: Found: C, 49.83; H, 5.07; N, 17.38; Cl, 14.34%.

EXAMPLE 3 dl-3-(2-Hydroxy-2-phenylethyl)-N-[(phenylamino)carbonyl]sydnone imine

Stir dl-5-amino-3-(2-hydroxy-2-phenylethyl)-1,2,3-oxadiazolium chloride (4.24 g.; 0.0176 moles) and isopropanol (15 ml), cool to −10° C. and add anhydrous sodium acetate (1.45 g.; 0.0176 mole). Stir for 20 minutes then drip in phenyl isocyanate (2.0 ml) over 15 minutes. Stir for 3 hours allowing the reaction to warm to room temperature. Filter the resulting solid, dissolve it in methylene chloride-methanol, treat with decolorizing charcoal then filter and replace the solvents with isopropanol by boiling on the steam-bath. Let stand to crystallize then filter to obtain 3.15 g. of the pure title product, m.p. = 187°–189° C. (dec.).

Analysis for: $C_{17}H_{16}N_4O_3$: Calculated: C, 62.95; H, 4.97; N, 17.28%: Found: C, 63.00; H, 5.09; N, 17.06%.

Activity Counts: 604 ($p < 0.01$) at 10 mg/kg., p.o.

EXAMPLE 4 dl-3-(2-Hydroxy-2-phenylpropyl)-N-[(phenylamino)carbonyl]sydnone imine

Dissolve dl-2-hydroxy-2-phenyl-propylamine, hydrochloride (9.4 g) in water (20 ml), stir and cool under nitrogen with an ice-bath. Add 37% aqueous formaldehyde solution (8.1 g), stir for ½ hour, then add a solution of potassium cyanide (3.3 g) in water (80 ml) dropwise. Stir and cool a further 1 hour, then add 5 N aqueous HCl (10 ml) followed by dropwise addition of a solution of sodium nitrite (3.45 g) in water (30 ml). Add another 20 ml of 5 N aqueous HCl solution followed by dropwise addition of a solution of sodium nitrite (3.45 g) in water (40 ml). Stir at 0° C. for 45 minutes then extract the reaction mixture with methylene chloride. Wash the extract with saturated sodium bicarbonate solution, brine and dry. Evaporate the solvents in vacuo to obtain 10.1 g. of dl-[(2-hydroxy-2-phenylpropyl)nitrosamino]acetonitrile, m.p. 89°–90° C.

Mix dl-[(2-hydroxy-2-phenylpropyl)nitrosamino]acetonitrile (5.0 g) with toluene (30 ml), add phenyl isocyanate (2.8 g) and triethylamine (2.3 g) using toluene rinses. Heat the reaction with stirring to 50°–60° C. for 5 hours, then let cool and stand overnight. Filter the crude product to obtain 4.85 g; m.p. 164°–165° C. Dissolve the solid in acetone, treat the solution with decolorizing carbon, filter, then replace the solvent with isopropanol by boiling in the steam-bath. Let cool to crystallize then filter to obtain 3.26 g of the pure title product; m.p. 167°–168° C.

Analysis for: $C_{18}H_{18}N_4O_3$: Calculated: C, 63.89; H, 5.36; N, 16.56%: Found: C, 63.51; H, 5.40; N, 16.55%.

Activity Counts: 977 ($p < 0.01$) at 10 mg/kg., p.o.

EXAMPLE 5 dl-N-[[(4-Chlorophenyl)amino]carbonyl]-3-(2-hydroxy-2-phenylpropyl)sydnone imine, hydrochloride Mix dl-[(2-hydroxy-2-phenylpropyl)nitrosamino]acetonitrile (4.5 g) prepared in Example 4 with toluene (46 ml) followed by 4-chlorophenylisocyanate (3.13 g) and triethylamine (2.02 g) and swirl, then heat the mixture with stirring to 50°–60° C. for 6 hours. Cool and stir at room temperature overnight. Filter the crude product to obtain 3.71 g. Suspend the solid (3.2 g) in ethyl acetate, add 5 N-isopropanolic-HCl (5.0 ml), stir to give a white solid. Filter and dry to obtain 1.00 g of the title product; m.p. 166° C. (dec.).

Analysis for: $C_{18}H_{17}ClN_4O_3 \cdot HCl$: Calculated: C, 52.82; H, 4.43; N, 13.69%: Found: C, 52.59; H, 4.65; N, 13.49%.

Activity Counts: 1052 ($p < 0.01$) at 1 mg/kg., p.o.; −394 ($p < 0.01$) at 10 mg/kg., p.o.

Conventional resolution of the racemic mixture yields the pure d and l-enantiomorphs.

EXAMPLE 6

1-5-Amino-3-(2-hydroxy-2-phenylethyl)-1,2,3-oxadiazolium chloride

Cover 1-2-amino-1-phenylethanol (20.17 g; 0.147 moles obtained as described in United Kingdom Pat. No. 1,097,074) with water (240 ml), stir and cool then add 5 N aqueous HCl (30 ml; 0.15 mole) and continue stirring until clear. Continue cooling and add 37% aqueous formaldehyde solution (15 ml) and follow by dripping in a solution of potassium cyanide (9.58 g.; 0.147 mole) in water (80 ml). Add diethyl ether to aid stirring, remove the cold-bath and continue stirring at room temperature for 3 hours. Let stand overnight then extract with diethyl ether. Wash, dry and evaporate the solvent in vacuo. Dissolve the resulting oil in diethyl ether, treat with decolorizing charcoal, filter and evaporate the ether in vacuo to obtain 1-[(2-hydroxy-2-phenylethyl)amino]acetonitrile as an oil. Dissolve the oil in water (100 ml) containing 5 N aqueous HCl (118 ml; 0.59 moles) and stir with cooling to $-10°$ C. Drip in a solution of sodium nitrite (20.29 g.; 0.294 moles) in water (100 ml) with stirring and cooling. Stir a further 3 hours at room temperature, add brine and extract with diethyl ether. Wash, dry and evaporate the extract in vacuo. Dissolve the residue in diethyl ether, treat with charcoal, filter and evaporate the ether in vacuo to obtain 1-N-nitroso-N-(2-hydroxy-2-phenylethyl)amino acetonitrile as an oil. Dissolve the oil in ethyl acetate, add excess 5 N-isopropanolic-HCl (30 ml). Filter the resulting solid to get 11.8 g. of title product, m.p.=192°–199° C. (dec.).

Dissolve 4.50 g. of the solid in methylene chloride-methanol, treat with decolorizing charcoal, filter and replace the solvents with isopropanol by boiling on the steam-bath. Cool and let stand to crystallize then filter to obtain 3.10 g. of the pure title product, m.p.=202°–206° C. (dec); $[\alpha]_D^{26} = -101.6°$ (1.075% in methanol).

Analysis for: $C_{10}H_{12}ClN_3O_2$: Calculated: C, 49.69; H, 5.01; N, 17.39; Cl, 14.67%: Found: C, 49.55; H, 5.04; N, 17.50; Cl, 14.63%.

EXAMPLE 7

1-[(2-Hydroxy-2-phenylethyl)nitrosamino]acetonitrile

The title compound, prepared as an oil in the preceding example may be prepared as a solid as follows:

Dissolve 1-2-hydroxy-2-phenylethylamine, hydrochloride (44.2 g) in water (300 ml), cool with an ice-bath then stir under nitrogen and add 37% aqueous formaldehyde solution (26 ml). Stir for 10 minutes then add a solution of potassium cyanide (16.6 g) in water (80 ml) dropwise with stirring. Stir a further 3 hours at room temperature then let stand overnight. Cool the reaction mixture with an ice-salt bath to 0°–5° C., then add 5 N aqueous HCl dropwise (153 ml) with stirring. Continue cooling and stirring and add a solution of sodium nitrite (35.2 g) in water (100 ml) dropwise. Remove the ice-bath and continue stirring at room temperature for 3 hours. Add ether and let stand overnight.

Extract the mixture well with methylene chloride then wash the extract with water, saturated sodium bicarbonate solution, brine and dry. Evaporate the solvent in vacuo and pump to get 42.0 g of the oily title product which crystallizes on standing. The product is sufficiently pure at this stage to use for subsequent reactions.

Remove a sample of the crude product (3.419 g) and triturate with cyclohexane containing a little ether. Decant, then triturate the solid with toluene and filter to obtain 0.991 g; m.p. 60°–62° C. Dissolve the solid in methylene chloride, treat with decolorizng carbon, filter and evaporate the solvent in vacuo. Triturate the crystalline solid with cyclohexane and filter to obtain 0.923 g of the pure title product; m.p. 61°–63° C.; $[\alpha]_D^{25} = -49.07°$ (1.00% in methanol).

Analysis for: $C_{10}H_{11}N_3O_2$: Calculated: C, 58.53; H, 5.40; N, 20.48%: Found: C, 58.38; H, 5.38; N, 20.95%.

EXAMPLE 8

1-3-(2-Hydroxy-2-phenylethyl)-N-[(phenylamino)carbonyl]sydnone imine

Stir 1-5-amino-3-(2-hydroxy-2-phenylethyl)-1,2,3-oxadiazolium chloride, prepared in Example 6, (6.04 g.; 0.025 moles) with isopropanol (40 ml) then cool with an ice-bath. Add anhydrous sodium acetate (2.05 g.; 0.025 moles) then with stirring and cooling drip in phenylisocyanate (2.72 ml). Continue stirring at room temperature for 5 hours then let stand overnight. Filter to obtain 6.7 g. of crude title product. Dissolve the solid in methylene chloride-methanol, treat with decolorizing charcoal, filter and replace the solvent with isopropanol by boiling on the steam bath. Let cool then filter to obtain 4.43 g. of the title product, m.p.=157°–161° C. Repeat the purification by dissolving the solid in chloroform-acetone, treating with decolorizing charcoal then filtering and evaporating the solvents in vacuo. Crystallize from isopropanol-diethyl ether and filter to obtain 2.76 g. of the pure title product, m.p. 158°–160° C., $[\alpha]_D^{25.5°} = -129.58°$ (0.885% in methanol).

Analysis for: $C_{17}H_{16}N_4O_3$: Calculated: C, 62.95; H, 4.97; N, 17.28%: Found: C, 62.65; H, 4.99; N, 17.36%.

Activity Counts: 1294 (p<0.01) at 10 mg/kg., p.o.

EXAMPLE 9

1-3-(2-Hydroxy-2-phenylethyl)-N-[(4-chlorophenylamino)carbonyl]sydnone imine Stir 1-5-amino-5-(2-hydroxy-2-phenylethyl)-1,2,3-oxadiazolium chloride (15.5 g) with isopropanol (150 ml), cool with an ice-salt bath then add anhydrous, powdered sodium acetate (5.79 g) followed by 4-chlorophenyl-isocyanate (10.83 g). Stir cold for 3 hours, then at room temperature for 2 hours. Filter and dry to obtain 18.1 g of crude product. Stir the solid with water (150 ml) for 2 hours, then filter and dry to obtain 13.99. g. Boil the solid with methylene chloridemethanol-acetone until nearly clear, filter then replace the solvent with isopropanol by boiling on the steambath. Let cool, reduce the volume further by evaporation in vacuo, then filter to obtain 11.17 g of pure title product; m.p. 191°–194° C. (dec); $[\alpha]_D^{25} = -73.06°$ (10.085% in DMF).

Analysis for: $C_{17}H_{15}ClN_4O_3$: Calculated: C, 56.91; H, 4.21; N, 15.62%: Found: C, 56.79; H, 4.41; N, 15.84%.

Activity Counts: 1375 (p<0.01) at 10 mg/kg., p.o.; 746 (p<0.01) at 1 mg/kg., p.o.

EXAMPLE 10

1-threo-5-amino-3-(2-hydroxy-1-methyl-2-phenylethyl)-1,2,3-oxadiazolium chloride Dissolve 1-threo-norpseudoephedrine hydrochloride (37.5 g.) in water (300 ml), cool then add 5 N aqueous HCl (40 ml) and 37% aqueous formaldehyde solution (20 ml). With stirring and cooling add a solution of potassium cyanide (13.0 g) in water (100 ml) dropwise. Stir cold 30 min. then drip in a solution of sodium nitrite (22.1 g) in water (100 ml) keeping the temperature below 6° C. Stir a further 10 min. then add diethyl ether then wash, dry and evaporate the extract in vacuo. Dissolve the remaining oil in ethyl acetate, add 5 N isopropanolic-HCl (32 ml) and allow to stand. Filter to obtain 18.7 g. of title product, m.p. 213°–215° C. $[\alpha]_D^{25} = -138.07°$ (1% in methanol).

Analysis for: $C_{11}H_{14}ClN_3O_2$: Calculated: C, 51.67; H, 5.52; N, 16.43; Cl, 13.86%: Found: C, 51.41; H, 5.53; N, 16.04; Cl, 13.49%.

EXAMPLE 11 l-threo-3-(2-Hydroxy-1-methyl-2-phenylethyl)-N-[(phenylamino)carbonyl]sydnone imine Stir l-threo-5-amino-3-(2-hydroxy-1-methyl-2-phenylethyl)-1,2,3-oxadiazolium chloride (5.114 g; 0.02 mole) with isopropanol (35 ml), cool and add anhydrous sodium acetate (1.64 g; 0.02 mole) followed in 15 min. by phenylisocyanate (2.38 g; 2.17 ml; 0.02 mole). Stir at room temperature for 3 hours. Filter to obtain 6.006 g. of crude title product, m.p. 167°–169° C. (dec). Dissolve the solid in methylene chloride-methanol, treat with charcoal, filter then replace the solvents with isopropanol by boiling. Let stand then filter to obtain 2.918 g. of pure title product, m.p. 188°–190° C. (dec); $[\alpha]_D^{25} = -218.52°$ (1.045% in methanol).

Analysis for: $C_{18}H_{18}N_4O_3$: Calculated: C, 63.89; H, 5.36; N, 16.56%: Found: C, 63.47; H, 5.39; N, 16.47%.

Activity Count: 856 (p<0.01) at 10 mg/kg., p.o.

EXAMPLE 12 l-threo-3-(2-Hydroxy-1-methyl-2-phenylethyl)-N-[(4-chlorophenylamino)carbonyl]sydnone imine Stir l-threo-5-amino-3-(2-Hydroxy-1-methyl-2-phenylethyl)-1,2,3-oxadiazolium chloride (3.84 g) with methanol (30 ml), cool and add anhydrous sodium acetate (1.23 g) followed in 10 minutes by 4-chlorophenylisocyanate (2.30 g). Stir at room temperature for 3 hours. Evaporate the solvent in vacuo and triturate the solid with water and ether and filter to get 2.17 g. of crude product. Boil the solid with a mixture of chloroform and acetone, filter and evaporate the filtrate in vacuo. Treat the resulting solid in methylene chloride-methanol with decolorizing charcoal, filter and replace the solvents with isopropanol by boiling. Let cool to crystallize then filter to obtain 0.978 g. of pure title product, m.p.=186°–188° C., $[\alpha]_D^{26} = -240.56°$ (1.52% in methanol).

Analysis for: $C_{18}H_{17}ClN_4O_3$: Calculated: C, 57.99; H, 4.60; N, 15.03%: Found: C, 57.88; H, 4.64; N, 15.06%.

Activity Count: 875 (p<0.005) at 10 mg/kg., p.o.; 731 (p<0.05) at 1 mg/kg., p.o.

The compounds in the following examples were prepared following the procedure of Example 9 with the exception that the appropriately substituted phenylisocyanate was employed.

EXAMPLE 13 l-N-[[(4-Fluorophenyl)amino]carbonyl]-3-(2-hydroxy-2-phenylethyl)sydnone imine

Melting point 181°–183° C.; $[\alpha]_D^{22.5} = -120.52$ (1.005% in methanol)

Analysis for: $C_{17}H_{15}FN_4O_3$: Calculated: C, 59.64; H, 4.42; N, 16.37%: Found: C, 59.38; H, 4.47; N, 16.50%.

Activity Count: 871 (p<0.01) at 10 mg/kg., p.o. 1152 (p<0.01) at 1 mg/kg., p.o.

EXAMPLE 14 l-N-[[(3,4-Dichlorophenyl)amino]carbonyl]-3-(2-hydroxy-2-phenylethyl)sydnone imine Melting point 185°–186.5° C. (dec); $[\alpha]_D^{22.5} = -104.97°$ (1.05% in 1:1 chloroform-methanol).

Analysis for: $C_{17}H_{14}Cl_2N_4O_3$: Calculated: C, 51.92; H, 3.59; N, 14.25%: Found: C, 51.75; H, 3.66; N, 14.37%.

Activity Count: 1215 (p<0.01) at 10 mg/kg., p.o. 65 (N.S.) at 1 mg/kg., p.o.

EXAMPLE 15 l-3-(2-Hydroxy-2-phenylethyl)-N-[[(4-nitrophenyl)amino]carbonyl]sydnone imine

Melting point 214.5°–216.5° C. (dec); $[\alpha]_D^{25} = -77.89°$ (0.97% in dimethylformamide).

Analysis for: $C_{17}H_{15}N_5O_5$: Calculated: C, 55.28; H, 4.09; N, 18.95%: Found: C, 55.02; H, 4.19; N, 19.06%.

Activity Count: 886 (p<0.01) at 10 mg/kg., 439 (p<0.05) at 1 mg/kg., p.o.

EXAMPLE 16 l-N-[[(4-Acetylphenyl)amino]carbonyl]-3-(2-hydroxy-2-phenylethyl)sydnone imine

Melting point 182°–184° C; $[\alpha]_D = -131.2°$ (1.01% in methanol).

Analysis for: $C_{19}H_{18}N_4O_4$: Calculated: C, 62.29; H, 4.95; N, 15.29%: Found: C, 62.21; H, 4.93; N, 15.42%.

Activity Count: 476 (p<0.01) at 10 mg/kg., p.o. −30 (N.S.) at 1 mg/kg., p.o.

What is claimed is:

1. A compound of the formula:

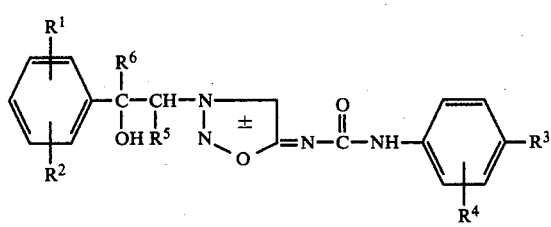

in which the enantiomeric form is d,l or l- when $R^5$ is hydrogen, and d,l or l-threo when $R^5$ is other than hydrogen;

$R^1$ and $R^2$ are, independently, hydrogen, alkyl of 1 to 6 carbon atoms, alkoxy of 1 to 6 carbon atoms, halo or trifluoromethyl;

$R^3$ is hydrogen, halo, nitro or alkanoyl of 2 to 4 carbon atoms;

$R^4$ is hydrogen or halo;

$R^5$ and $R^6$ are, independently, hydrogen or methyl; or a non-toxic acid addition salt thereof.

2. A compound of claim 1 of the formula:

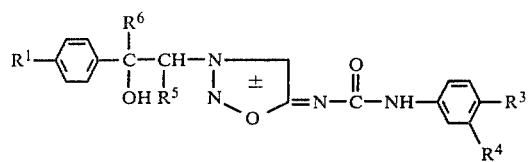

in which the enantiomeric form is l- when $R^5$ is hydrogen and l-threo when $R^5$ is other than hydrogen;

$R^1$ is hydrogen, alkyl of 1 to 6 carbon atoms, alkoxy of 1 to 6 carbon atoms, halo or trifluoromethyl;

$R^3$ is hydrogen, halo, nitro or alkanoyl of 2 to 4 carbon atoms;

$R^4$ is hydrogen or halo;

$R^5$ and $R^6$ are, independently, hydrogen or methyl; or a non-toxic acid addition salt thereof.

3. An l-enantiomorph of claim 1 of the formula:

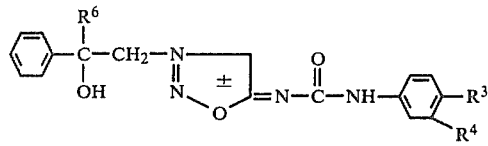

in which $R^3$ is hydrogen, halo, nitro or alkanoyl of 2 to 4 carbon atoms;

$R^4$ is hydrogen or halo;

$R^6$ is hydrogen or methyl; or a non-toxic acid addition salt thereof;

4. An l-threo enantiomorph of claim 1 of the formula:

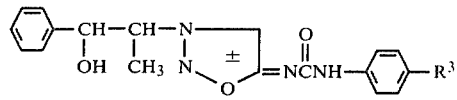

in which $R^3$ is hydrogen, halo, nitro or alkanoyl of 2 to 4 carbon atoms;

or a non-toxic acid addition salt thereof.

5. The compounds of claim 1 which are dl-3-(2-hydroxy-2-phenylethyl)-N-[(phenylamino)carbonyl]-sydnone imine.

6. The compound of claim 1 which is l-3-(2-hydroxy-2-phenylethyl)-N-[(phenylamino)carbonyl]sydnone imine.

7. The compound of claim 1 which is l-3-(2-hydroxy-2-phenylethyl)-N-[(4-chlorophenylamino)carbonyl]-sydnone imine.

8. The compound of claim 1 which is l-threo-3-(2-hydroxy-1-methyl-2-phenylethyl)-N-[(phenylamino)-carbonyl]sydnone imine.

9. The compound of claim 1 which is l-threo-3-(2-hydroxy-1-methyl-2-phenylethyl)-N-[(4-chloro-phenylamino)carbonyl]sydnone imine.

10. The compounds of claim 1 which are dl-3-(2-hydroxy-2-phenylpropyl)-N-[(phenylamino)carbonyl]-sydnone imine.

11. The compounds of claim 1 which are dl-N-[[(4-chlorophenyl)amino]carbonyl]-3-(2-hydroxy-2-phenyl-propyl)sydnone imine.

12. The compound of claim 1 which is l-N-[[(4-fluorophenyl)amino]carbonyl]-3-(2-hydroxy-2-phenylethyl)-sydnone imine.

13. The compound of claim 1 which is l-N-[[(3,4-dichlorophenyl)amino]carbonyl]-3-(2-hydroxy-2-phenylethyl)sydnone imine.

14. The compound of claim 1 which is l-3-(2-hydroxy-2-phenylethyl)-N-[[(4-nitrophenyl)amino]carbonyl]sydnone imine.

15. The compound of claim 1 which is l-N-[[(4-acetylphenyl)amino]carbonyl]-3-(2-hydroxy-2-phenylethyl)-sydnone imine.

* * * * *